(12) United States Patent
Saitou et al.

(10) Patent No.: US 9,389,146 B2
(45) Date of Patent: Jul. 12, 2016

(54) MALFUNCTION-DETERMINING DEVICE FOR EXHAUST GAS PURIFYING DEVICE AND MALFUNCTION-DETERMINING METHOD FOR EXHAUST GAS PURIFYING DEVICE

(71) Applicant: KOMATSU LTD., Minato-ku, Tokyo (JP)

(72) Inventors: Shinichi Saitou, Oyama (JP); Shouhei Nagasaka, Oyama (JP); Mitsuyoshi Kimura, Oyama (JP); Ken Nakano, Oyama (JP)

(73) Assignee: Komatsu Ltd., Tokyo (JP)

( * ) Notice: Subject to any disclaimer, the term of this patent is extended or adjusted under 35 U.S.C. 154(b) by 21 days.

(21) Appl. No.: 14/368,880

(22) PCT Filed: Feb. 26, 2014

(86) PCT No.: PCT/JP2014/054713
§ 371 (c)(1),
(2) Date: Jun. 26, 2014

(87) PCT Pub. No.: WO2015/128970
PCT Pub. Date: Sep. 3, 2015

(65) Prior Publication Data
US 2015/0240696 A1    Aug. 27, 2015

(51) Int. Cl.
*G01M 13/00* (2006.01)
*G01M 15/10* (2006.01)
(Continued)

(52) U.S. Cl.
CPC ........... *G01M 15/106* (2013.01); *F02D 41/148* (2013.01); *F02D 41/222* (2013.01);
(Continued)

(58) Field of Classification Search
CPC . F01N 11/00; F01N 2560/05; F02D 41/1466; F02D 41/222; G01M 15/04; G01N 15/06; G06F 15/00; Y02T 10/40; Y02T 10/47
USPC ........... 73/1.58, 23.33, 75, 76, 114; 701/29.1, 701/29.7, 30.2, 30.5, 31.1, 31.2, 99, 101, 701/107; 340/436; 60/272–324; 123/672–703
See application file for complete search history.

(56) References Cited

U.S. PATENT DOCUMENTS 6,192,866 B1 * 2/2001 Araki .................... F02D 41/222
                                                  123/479
7,404,291 B2 * 7/2008 Endo ....................... F01N 3/035
                                                    60/274
(Continued)

FOREIGN PATENT DOCUMENTS

CN        102906382        3/2013
EP       1975396 A1       10/2008
(Continued)

OTHER PUBLICATIONS

Office Action issued Sep. 24, 2014 in corresponding Japanese Patent Application No. 2014-530041, including English translation, 5 pages.

(Continued)

*Primary Examiner* — Hezron E Williams
*Assistant Examiner* — Gedeon M Kidanu
(74) *Attorney, Agent, or Firm* — Fish & Richardson P.C.

(57) ABSTRACT

A malfunction-determining device for an exhaust gas purifying device, which includes a filter device and a pressure measuring device, includes a usability determiner being configured to determine whether or not the pressure measuring device is usable based on a pressure measured by the pressure measuring device and an exhaust gas flow rate, a frozen-state determiner being configured to determine whether or not the pressure measuring device is frozen, and a malfunction determiner being configured to determine that the pressure measuring device has a malfunction when the usability determiner determines that the pressure measuring device is unusable and the frozen-state determiner determines that the pressure measuring device is not frozen.

6 Claims, 6 Drawing Sheets

(51) Int. Cl.
*F02D 41/14* (2006.01)
*F02D 41/22* (2006.01)
*G01N 7/00* (2006.01)
*F02D 41/02* (2006.01)

(52) U.S. Cl.
CPC ......... *G01M13/005* (2013.01); *F02D 41/029* (2013.01); *F02D 41/1445* (2013.01); *F02D 2200/0812* (2013.01); *G01N 7/00* (2013.01); *Y02T 10/40* (2013.01); *Y02T 10/47* (2013.01)

(56) References Cited

U.S. PATENT DOCUMENTS

| | | | | |
|---|---|---|---|---|
| 2006/0288693 | A1* | 12/2006 | Endo | F01N 3/035 60/297 |
| 2007/0251214 | A1* | 11/2007 | Nishino | F01N 11/00 60/277 |
| 2009/0193904 | A1* | 8/2009 | Takahashi | B01D 46/0086 73/716 |
| 2011/0100094 | A1* | 5/2011 | Konrad | F01N 11/002 73/28.04 |
| 2011/0232364 | A1* | 9/2011 | Koizumi | B01D 46/0057 73/23.33 |
| 2012/0192635 | A1* | 8/2012 | Ide | F01N 11/002 73/114.76 |
| 2013/0014641 | A1* | 1/2013 | Takaoka | F01N 3/0253 95/26 |
| 2013/0068107 | A1 | 3/2013 | Haseyama et al. | |
| 2014/0318105 | A1* | 10/2014 | Keppeler | F02D 41/029 60/274 |

FOREIGN PATENT DOCUMENTS

| | | |
|---|---|---|
| EP | 2305977 A1 | 6/2012 |
| JP | H11-132026 A | 5/1999 |
| JP | 2007002694 A | 1/2007 |
| JP | 2008215535 A | 9/2008 |
| JP | 2008111409 A1 | 6/2010 |
| JP | 2011069259 A | 4/2011 |
| JP | 2013002366 A | 1/2013 |
| JP | 2013122182 A | 6/2013 |
| JP | 2013253544 A | 12/2013 |

OTHER PUBLICATIONS

International Search Report issued Apr. 15, 2014 in International Application No. PCT/JP2014/054713, 9 pages.
Office Action issued Mar. 18, 2016 in corresponding Chinese Patent Application No. 201480000359.7, including English Translation, 7 pages.

* cited by examiner

MALFUNCTION-DETERMINING DEVICE FOR EXHAUST GAS PURIFYING DEVICE AND MALFUNCTION-DETERMINING METHOD FOR EXHAUST GAS PURIFYING DEVICE

CROSS-REFERENCE TO RELATED APPLICATIONS

This application claims priority to International Application No. PCT/JP2014/054713 filed on Feb. 26, 2014, the contents of which application are incorporated herein by reference in its entirety.

TECHNICAL FIELD

The present invention relates to a malfunction-determining device for an exhaust gas purifying device and a malfunction-determining method for an exhaust gas purifying device.

BACKGROUND ART

Nowadays, vehicles/machines equipped with an internal combustion engine (e.g., a diesel engine) such as construction machines (e.g., hydraulic excavator and wheel loader), haulage vehicles (e.g., bus, freight truck, dump truck and on-road truck), and fixed power generators are provided with an exhaust gas purifying device in which particulate matter (PM) in exhaust gas from the internal combustion engine is removed through a diesel particulate filter (DPF). The exhaust gas purifying device is equipped with a pressure sensor (differential-pressure sensor) that detects a differential pressure in a filter used as the DPF between an inlet-side pressure and an outlet-side pressure of exhaust gas. Based on the differential pressure detected by the pressure sensor, the amount of PM deposited on the filter is estimated. For instance, Patent Literatures 1 and 2 disclose arrangements configured to determine a malfunction of a pressure sensor or a pressure-introducing hose connected to the pressure sensor.

Specifically, according to Patent Literature 1, it is determined whether or not there is a problem (i.e., hose damage) with a pressure-introducing hose connected to a pressure sensor for a DPF based on: a determination result on a malfunction of the DPF based on an inlet-side temperature and outlet-side temperature of exhaust gas in the filter; and a differential pressure detected by the pressure sensor.

According to Patent Literature 2, a duct connected to an outlet side of a filter is provided with a switch valve so that the filter can be exposed to atmospheric air and it is determined whether or not there is a malfunction of a pressure sensor based on a change in pressure at an upstream side of the filter when the filter is exposed to atmospheric air.

Thus, according to Patent Literatures 1 and 2, when it is determined that pressure is improperly introduced into the pressure sensor or the pressure sensor itself has a malfunction, a report on the malfunction is made to notify an operator of the malfunction. The operator may then call a serviceperson and ask him/her to do maintenance such as replacement of the pressure sensor or the hose.

CITATION LIST

Patent Literatures

Patent Literature 1: JP-A-2013-2366
Patent Literature 2: JP-A-2008-111409

SUMMARY OF THE INVENTION

Problem(s) to be Solved by the Invention

For instance, when a vehicle or machine is operated in a cold region and an engine therein is started at a low temperature, a malfunction of a pressure sensor of an exhaust gas purifying device is sometimes reported. In this case, an operator stops the operation of the construction machine and asks a serviceperson to do inspection.

However, it has been found that a malfunction of a pressure sensor at the start-up of an engine at a low temperature is usually not attributed to a failure in the pressure sensor itself but to improper introduction of pressure into the pressure sensor due to freezing of condensation water in a pressure-introducing duct. In such a case, the frozen condensation water is usually getting gradually unfrozen with an increase in outside air temperature as time elapses and/or with an increase in the temperature of the exhaust gas purifying device heated by exhaust gas in operation, thereby letting pressure into the pressure sensor, so that the function of the pressure sensor gets recovered to eliminate the malfunction.

However, Patent Literatures 1 and 2 are silent about a malfunction of a pressure sensor due to freezing and thus the malfunction would be reported upon determination of the occurrence of a malfunction irrespective of what causes the malfunction. Therefore, even though it is highly possible that the malfunction is eliminated by continuing the ongoing operation, a serviceperson is called and a vehicle or a machine is stopped for inspection, which results in lowering the operation rate of the vehicle or machine.

An object of the invention is to provide a malfunction-determining device for an exhaust gas purifying device capable of determining whether or not a malfunction of a pressure sensor is caused by freezing to maintain the operation rate of a vehicle or a machine, and a malfunction-determining method for an exhaust gas purifying device.

Means for Solving the Problem(s)

According to an aspect of the invention, a malfunction-determining device for an exhaust gas purifying device, the exhaust gas purifying device including: a filter device being provided in an exhaust passage for exhaust gas exhausted from an internal combustion engine to remove a residual substance in the exhaust gas; and a pressure measuring device being provided to the filter device to measure a pressure of the exhaust gas, the malfunction-determining device includes: a usability determiner being configured to determine whether or not the pressure measuring device is usable based on the pressure measured by the pressure measuring device and an exhaust gas flow rate; a frozen-state determiner being configured to determine whether or not the pressure measuring device is frozen; and a malfunction determiner being configured to determine that the pressure measuring device has a malfunction when the usability determiner determines that the pressure measuring device is unusable and the frozen-state determiner determines that the pressure measuring device is not frozen.

According to the above arrangement, the usability determiner determines whether or not the pressure measuring device is usable. When the usability determiner determines that the pressure measuring device is unusable, the frozen-state determiner determines whether or not the pressure measuring device becomes unusable due to freezing. The pressure measuring device includes a pressure sensor and a pressure-introducing duct through which the pressure of exhaust gas or the like is introduced into the pressure sensor. When water vapor condenses in the pressure measuring device and the condensation water gets frozen in the pressure sensor and/or duct, the pressure cannot be led to the pressure sensor and thus the pressure measuring device cannot accurately measure the pressure of the exhaust gas or the like. Therefore, the pressure measuring device may be determined to be unusable not due to a failure in the pressure sensor or damage to the duct but rather due to freezing.

When the frozen-state determiner determines that the pressure measuring device is unusable due to freezing, the malfunction determiner may determine that repair or replacement of the pressure measuring device is unnecessary because the malfunction of the pressure measuring device is attributed not to a failure in the pressure sensor or damage to, for instance, the pressure-introducing duct into the pressure sensor but rather due to freezing, so that a normal function of the pressure measuring device will be recovered when the frozen part becomes unfrozen. In this case, the malfunction-determining device does not report the malfunction of the pressure measuring device to an operator, so that the operator can continue the use of the exhaust gas purifying device without calling a serviceperson.

On the other hand, when the pressure measuring device is unusable not due to freezing, the malfunction determiner determines that there is a problem with the pressure sensor itself or the duct etc. The malfunction-determining device may then report the malfunction to an operator to repair or replace the pressure sensor or the duct.

In short, the malfunction determiner determines that there is a malfunction of the pressure measuring device when the usability determiner determines that the pressure measuring device is unusable and the frozen-state determiner determines that the pressure measuring device is not frozen. Therefore, when the pressure measuring device is determined to be frozen, the malfunction determiner does not determine that there is a malfunction, so that the vehicle or machine can be kept in operation, thereby maintaining a favorable operation rate.

It is preferable that the malfunction-determining device for the exhaust gas purifying device include a malfunction notifier being configured to report the malfunction of the pressure measuring device when the malfunction determiner determines that the pressure measuring device has the malfunction.

According to the above arrangement, an operator can be notified of a malfunction of the pressure measuring device not due to freezing. Therefore, the operator can know that the pressure measuring device malfunctions for a reason other than freezing and thus can stop the vehicle or machine. In this manner, the exhaust gas purifying device can be prevented from being in operation when the pressure measuring device malfunctions.

In the malfunction-determining device for the exhaust gas purifying device, it is preferable that the pressure measuring device be configured to measure a differential pressure in a filter used in the filter device between an inlet-side pressure and an outlet-side pressure of the exhaust gas, and the usability determiner is configured to determine whether or not the pressure measuring device is usable based on the measured differential pressure and the exhaust gas flow rate.

An increase in the deposition amount of a collected residual substance such as PM results in clogging of the filter, so that the exhaust gas purifying device is subjected to a regeneration process, thereby burning the collected residual substance to unclog the filter. The deposition amount of the residual substance on the filter is usually estimated from the differential pressure measured by the pressure sensor of the pressure measuring device and an exhaust-gas flow rate. Therefore, when the pressure measuring device becomes unusable due to a malfunction therein or freezing, a value of the differential pressure becomes unusual for the exhaust-gas flow rate, so that the pressure measuring device can be easily determined to be unusable.

In the malfunction-determining device for the exhaust gas purifying device, it is preferable that the frozen-state determiner include a temperature sensor configured to measure an atmospheric temperature or a temperature of the pressure measuring device and determines that the pressure measuring device is not frozen when the temperature measured by the temperature sensor is higher than a predetermined temperature.

According to the above arrangement, the frozen-state determiner includes a temperature sensor for measuring atmospheric temperature or a temperature sensor for measuring the temperature of the pressure measuring device, and determines whether or not the temperature measured by the temperature sensor (i.e., the atmospheric temperature or the temperature of the pressure measuring device) is higher than a predetermined temperature. The predetermined temperature should be set at a low temperature at which condensation water is less likely to be frozen (e.g., 10 degrees C.) so that the pressure measuring device is not determined to be frozen as long as the measured temperature is higher than the predetermined temperature.

Incidentally, the temperature sensor for measuring the temperature of the pressure measuring device may be incorporated in the pressure measuring device at a portion where the pressure sensor is installed or in the duct, or may be installed in a space where the pressure measuring device is installed.

Further, the temperature sensor for measuring atmospheric temperature may be installed anywhere in a vehicle body or the like where the temperature sensor is less likely to be affected by heat from the internal combustion engine. The pressure measuring device is possibly frozen when atmospheric temperature is low and thus the exhaust gas purifying device and the pressure measuring device are cooled by the atmosphere while the vehicle or machine is not in operation. In view of the above, as long as atmospheric temperature is not lower than a temperature at which the pressure measuring device is less likely to be frozen (e.g., 10 degrees C.), the pressure measuring device is not determined to be frozen. Therefore, even when the temperature of the pressure measuring device cannot be directly measured, it can be determined whether or not the pressure measuring device is possibly frozen by measuring atmospheric temperature.

In the malfunction-determining device for the exhaust gas purifying device, it is preferable that the frozen-state determiner include a timer being configured to measure time elapsed since the internal combustion engine is started and determines that the pressure measuring device is not frozen when the time measured by the timer exceeds a predetermined time.

According to the above arrangement, the frozen-state determiner includes a timer to measure time elapsed since the start of the engine and determines whether or not the measured time exceeds a predetermined time. The predetermined time should be set at a time sufficient for frozen condensation water in the pressure measuring device to be heated by the exhaust gas to get unfrozen (e.g., eight hours) so that even when the pressure measuring device is frozen, the pressure measuring device is not determined to be frozen as long as the measured time exceeds the predetermined time.

According to another aspect of the invention, a malfunction-determining method for an exhaust gas purifying device, the exhaust gas purifying device including: a filter device being provided in an exhaust passage for exhaust gas exhausted from an internal combustion engine to remove a residual substance in the exhaust gas; and a pressure measuring device being provided to the filter device to measure a pressure of the exhaust gas, the malfunction-determining method includes: determining whether or not the pressure measuring device is usable based on the pressure measured by the pressure measuring device and an exhaust gas flow rate; determining whether or not the pressure measuring device is frozen after the pressure measuring device is determined to be unusable; and determining that the pressure measuring device has a malfunction when the pressure measuring device is determined not to be frozen.

The malfunction-determining method according to the above aspect provides the same effects as those of the above malfunction-determining device. Specifically, even when the pressure measuring device is determined to be unusable, the vehicle or machine can be kept in operation as long as the pressure measuring device is determined to be frozen, thereby maintaining a favorable operation rate.

DESCRIPTION OF EMBODIMENT(S)

An exemplary embodiment of the invention will be described below with reference to the attached drawings.

Figure 1:
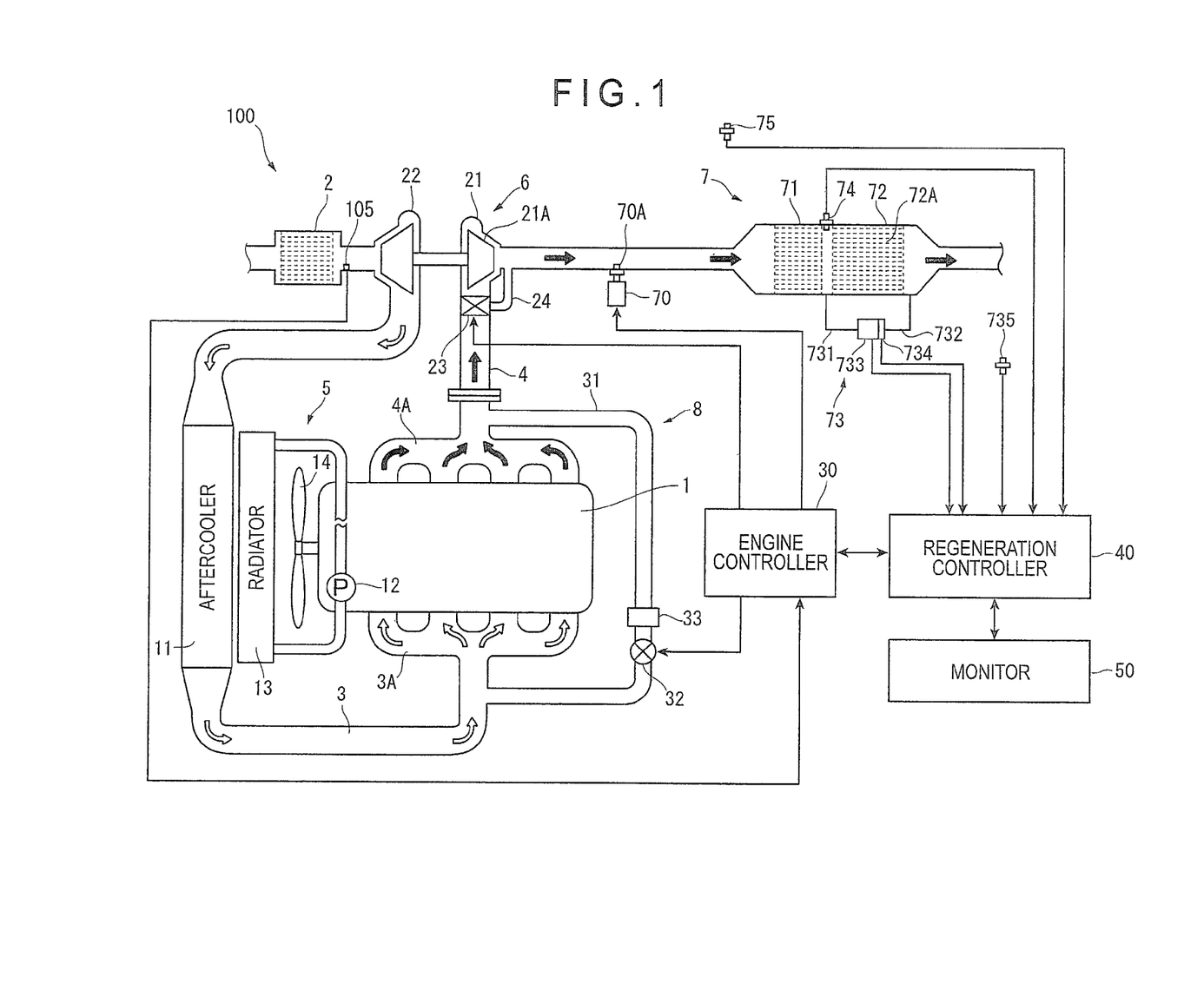
FIG. 1 schematically shows an internal combustion engine including a malfunction-determining device of an exhaust gas purifying device according to an exemplary embodiment of the invention.

FIG. 1 schematically shows an arrangement of a diesel engine 100 as an internal combustion engine including a malfunction-determining device of an exhaust gas purifying device according to the exemplary embodiment of the invention.

Schematic Description on Overall Arrangement of Diesel Engine

As shown in FIG. 1, the diesel engine 100 includes: an engine body 1 in which a plurality of combustion chambers are provided; an air cleaner 2 through which intake air is filtered to prevent foreign substances such as dust from entering the combustion chambers; an intake pipe 3 through which the intake air is supplied to the combustion chambers in the engine body 1; an exhaust pipe 4 through which exhaust gas is discharged from the combustion chambers in the engine body 1; a cooling system 5; a turbocharger 6; an exhaust gas purifying device 7; an exhaust-gas-recirculation system 8; an engine controller 30; a regeneration controller 40 serving as the malfunction-determining device; and a monitor 50.

The diesel engine 100 according to the exemplary embodiment is intended to be equipped to construction machines such as hydraulic excavator, wheel loader and off-road dump truck, which are non-exhaustive. For instance, the diesel engine 100 may be equipped to an on-road track or a fixed power generator.

An intake manifold 3A is attached between the engine body 1 and the intake pipe 3 so that the intake air supplied from the intake pipe 3 is distributed among the combustion chambers in the engine body 1. An exhaust manifold 4A interconnects the engine body 1 and the exhaust pipe 4 so that the exhaust gas discharged from each of the combustion chambers in the engine body 1 flows into the exhaust pipe 4 along with exhaust gas from the other combustion chambers.

The intake pipe 3 is provided with an aftercooler 11 to cool air compressed by the turbocharger 6. The cooling system 5 includes a pump 12 driven by, for instance, a crankshaft (not shown) housed in the engine body 1. Cooling water pumped by the pump 12 is air-cooled by a radiator 13 incorporated in the cooling system 5 after cooling parts to be cooled such as the engine body 1, the turbocharger 6 and an oil-cooler (not shown). The cooling performance of the aftercooler 11 and the radiator 13 is enhanced by a fan 14 provided to the engine body 1 and rotationally driven by, for instance, a crankshaft (not shown).

The turbocharger 6 includes: a turbine 21 inserted in the exhaust pipe 4; a compressor 22 inserted in the intake pipe 3 and connected to the turbine 21 to be driven;

and a variable geometry nozzle 23 that controls a flow rate of exhaust gas supplied to the turbine 21. The turbocharger 6 adjusts the opening degree of the variable geometry nozzle 23 to control the rotation speed of the turbine 21. The rotation of the turbine 21 drives the compressor 22 to supply air to the engine body 1. Incidentally, when the variable geometry nozzle 23 is fully closed, exhaust gas is discharged toward the exhaust gas purifying device 7 via a bypass 24. Specifically, while exhaust gas is supplied to a turbine disc 21A to work on the turbine disc 21A when the variable geometry nozzle 23 is opened, exhaust gas is discharged toward the exhaust gas purifying device 7 via the bypass 24 when the variable geometry nozzle 23 is fully closed, thereby making the exhaust gas less work on the turbine disc 21A to increase the temperature of the exhaust gas.

The exhaust gas purifying device 7, which is provided downstream of the turbine 21 to remove PM (residual substance) contained in exhaust gas, includes a diesel oxidation catalyst (DOC) 71, and a DPF 72 (a filter device), a pressure measuring device 73 and an exhaust-gas-temperature sensor 74. The DOC 71 and the DPF 72 are arranged in a cylindrical exhaust pipe such that the DOC 71 is provided near an upstream end of the exhaust pipe and the DPF 72 is provided near a downstream end of the exhaust pipe. A dosing nozzle 70A that injects a dosing fuel supplied from a dosing fuel supplier 70 is provided between the turbine 21 and the exhaust gas purifying device 7. The dosing fuel is injected when forcible regeneration is commanded. The dosing fuel is the same as a fuel for driving the diesel engine 100. Incidentally, instead of supplying the dosing fuel from the dosing fuel supplier 70, post-injection may be performed using a fuel injector configured to inject fuel into the combustion chambers.

The DOC 71, which is made of Pt (platinum) or the like, oxidizes CO (carbon monoxide) and HC (hydrocarbon) contained in exhaust gas and SOF (soluble organic fraction) contained in PM to remove them. Further, the DOC 71 oxidizes NO (nitrogen monoxide) contained in exhaust gas into $NO_2$ (nitrogen dioxide) and further oxidizes the dosing fuel injected from the dosing nozzle 70A, thereby increasing the temperature of the exhaust gas.

The DPF 72 includes a catalyzed soot filter (CSF) 72A that is a filter for collecting PM. A base of the CSF 72A is made of silicon carbide, alumina or the like. PM contained in exhaust gas is collected when passing through fine pores formed through the CSF 72A. As shown in FIG. 1, the CSF 72A has cells closely arranged in the cylindrical exhaust pipe, the cells defining fine flow passages extending along an exhaust-gas-flowing direction. Specifically, the CSF 72A is a wall-flow filter in which cells with closed upstream ends and cells with closed downstream ends are alternately arranged. The collected PM is oxidized (burnt) by oxygen contained in exhaust gas and $NO_2$ generated by the DOC 71 as long as the temperature of the exhaust gas is sufficient for PM to be oxidized.

The pressure measuring device 73 includes: a duct 731 connected to an upstream side of the CSF 72A; a duct 732 connected to a downstream side of the CSF 72A; a pressure sensor 733 that measures a differential pressure between an inlet-side pressure of exhaust gas introduced through the duct 731 and an outlet-side pressure of the exhaust gas introduced through the duct 732 and outputs the measured differential pressure (pressure) to the regeneration controller 40; and an outlet pressure sensor 734 that measures the pressure introduced through the duct 732 and outputs the measured pressure to the regeneration controller 40. Further, a vehicle body of a construction machine, on which the diesel engine 100 is mounted, is equipped with an atmospheric pressure sensor 735. The atmospheric pressure sensor 735 likewise outputs a measured pressure (i.e., atmospheric pressure) to the regeneration controller 40.

The exhaust-gas-temperature sensor 74, which is provided at an upstream side of the CSF 72A, detects a temperature of exhaust gas at an inlet of the CSF 72A and outputs the measured temperature (i.e., DPF temperature) to the regeneration controller 40.

The vehicle body of the construction machine is also equipped with an atmospheric-temperature sensor 75. The atmospheric-temperature sensor 75 measures atmospheric temperature outside the vehicle body and outputs the measured temperature (i.e., atmospheric temperature) to the regeneration controller 40.

The exhaust-gas-recirculation system 8 includes an exhaust gas recirculation line 31 through which the exhaust manifold 4A and the intake pipe 3 are in communication with each other. The exhaust gas from the exhaust manifold 4A is partly bypassed through the exhaust gas recirculation line 31 to be recirculated through the intake pipe 3. The exhaust gas recirculation line 31 is provided with an EGR valve 32 that opens and closes the exhaust gas recirculation line 31 and an EGR cooler 33 that cools the exhaust gas from the exhaust manifold 4A. The exhaust-gas-recirculation system 8 recirculates a part of the exhaust gas through the intake manifold 3A via the exhaust gas recirculation line 31 to lower the concentration of oxygen in the intake air and, consequently, decrease the combustion temperature of the engine body 1. This results in a decrease in the content of a nitrogen oxide in the exhaust gas.

The diesel engine 100 includes a flow rate sensor 105. The flow rate sensor 105, which is in the form of a mass flow sensor, detects an intake mass flow rate of the air supplied to the engine body 1 and inputs a signal representing the mass flow rate of the intake air to the engine controller 30.

Engine Controller

The engine controller 30 controls engine speed and torque by adjusting a fuel injection amount, a fuel injection timing, the EGR valve 32 and the variable geometry nozzle 23 in accordance with a value inputted to an input unit corresponding to an operator's request made through, for instance, an accelerator pedal (not shown). Further, the engine controller 30 controls forcible regeneration by: adjusting the fuel injection amount, the fuel injection timing, the EGR valve 32 and the variable geometry nozzle 23 to increase the temperature of the exhaust gas in accordance with a command from the regeneration controller 40; and injecting the dosing fuel from the dosing nozzle 70A. Especially, for the forcible regeneration control, the engine controller 30 closes the EGR valve 32 and the variable geometry nozzle 23 with the fuel injection amount adjusted to a low level, thereby increasing the temperature of the exhaust gas.

Regeneration Controller

Figure 2:
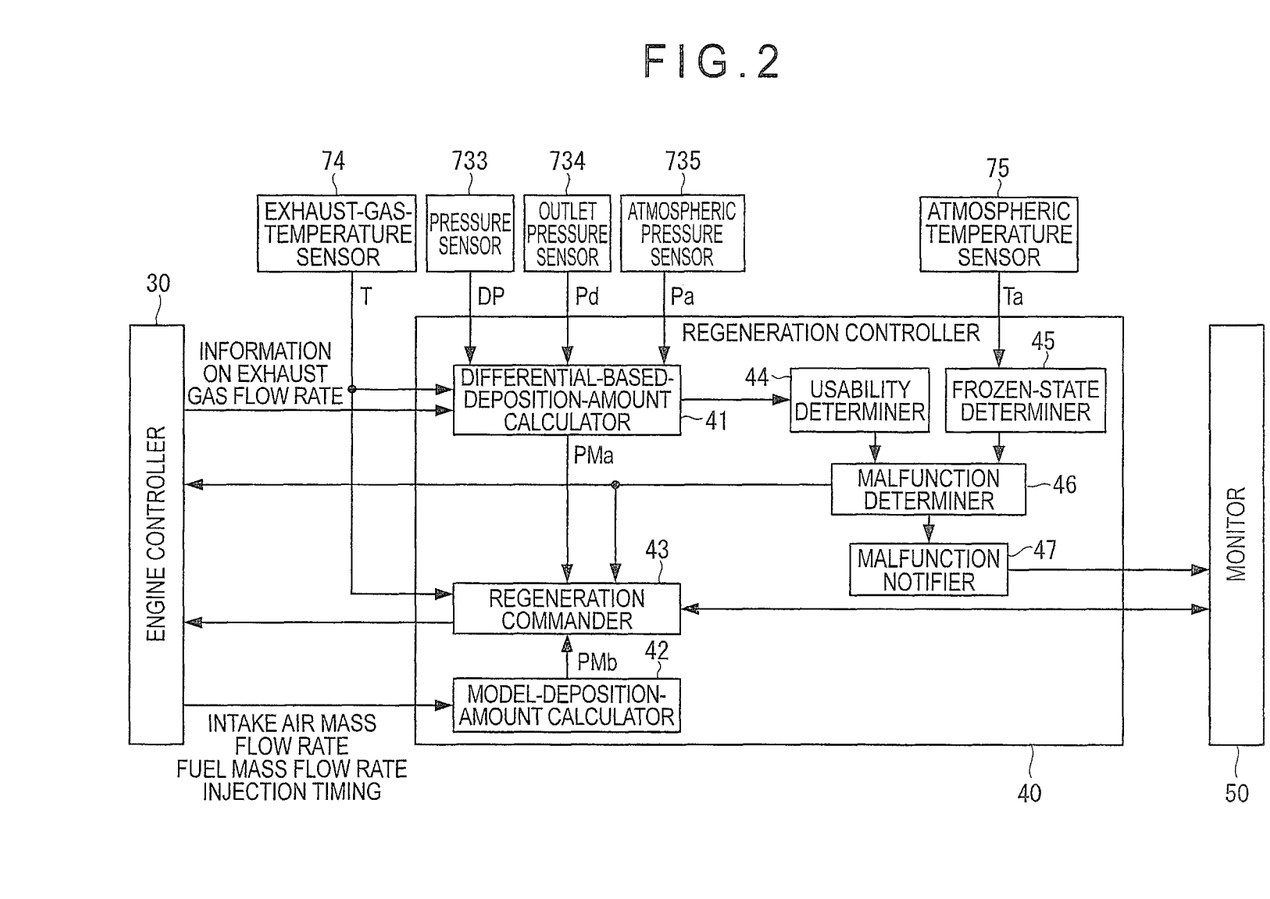
FIG. 2 is a block diagram showing the malfunction-determining device.

As shown in FIG. 2, the regeneration controller 40 includes a differential-based-deposition-amount calculator 41, a model-deposition-amount calculator 42, a regeneration commander 43, a usability determiner 44, a frozen-state determiner 45, a malfunction determiner 46 and a malfunction notifier 47.

The differential-based-deposition-amount calculator 41 or the model-deposition-amount calculator 42 of the regeneration controller 40 calculates an estimated value of the amount of PM deposited on the CSF 72A, and outputs a command for regenerating the CSF 72A to the engine controller 30 when the PM-deposition amount exceeds a predetermined threshold.

Further, when manual regeneration is commanded via the monitor 50, the regeneration controller 40 sends a command for manual forcible regeneration to the engine controller 30. When the manual forcible regeneration is completed, the regeneration controller 40 notifies an operator of the completion.

Further, the regeneration controller 40 determines whether or not the pressure measuring device 73 has a malfunction. When the pressure measuring device 73 is determined to have a malfunction, the regeneration controller 40 notifies an operator of the malfunction.

Incidentally, although FIG. 1 shows that the regeneration controller 40 is provided outside the engine controller 30, the regeneration controller 40 may be provided inside the engine controller 30.

Differential-Based-Deposition-Amount Calculator

The differential-based-deposition-amount calculator 41 is inputted with: a differential pressure DP measured by the pressure sensor 733 of the pressure measuring device 73; a DPF-downstream pressure Pd measured by the outlet pressure sensor 734; an atmospheric pressure Pa measured by the atmospheric pressure sensor 735; a DPF temperature T measured by the exhaust-gas-temperature sensor 74; and information on exhaust-gas flow rate outputted from the engine controller 30. The information on exhaust-gas flow rate includes an exhaust-gas mass flow rate m obtained by adding up the intake mass flow rate detected by the flow rate sensor 105 and a fuel mass flow rate estimated from the fuel injection amount. Based on the exhaust-gas mass flow rate m inputted from the engine controller 30, the DPF temperature T, a DPF-upstream pressure Pu, and a known gas constant R, the differential-based-deposition-amount calculator 41 calculates an exhaust-gas flow rate V to be inputted to the CSF 72A using the following state equation (1). The calculated exhaust-gas flow rate V is a volume flow rate.

$$Pu \cdot V = m \cdot R \cdot T \qquad (1)$$

Incidentally, the DPF-upstream pressure Pu is an absolute pressure obtained by adding up the atmospheric pressure Pa, the DPF-downstream pressure Pd (gauge pressure) and the differential pressure DP.

Figure 3:
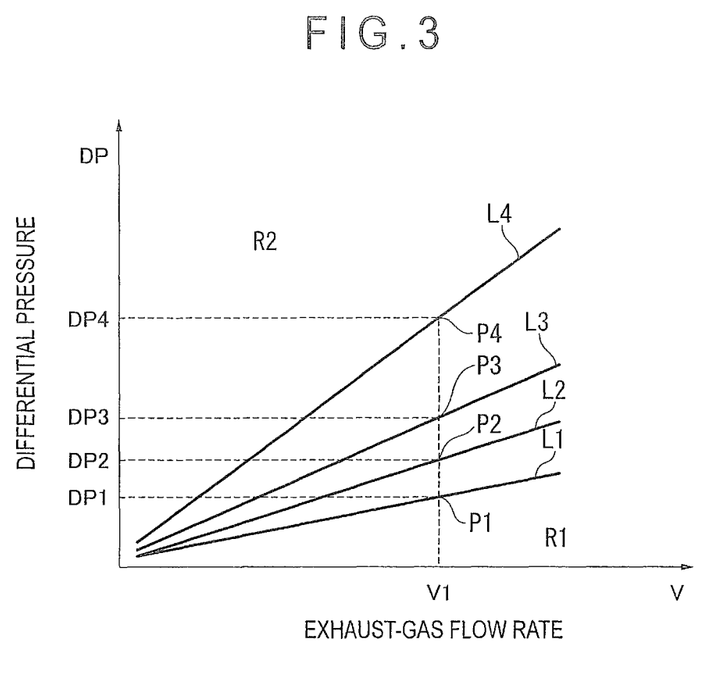
FIG. 3 shows a relationship among an exhaust-gas flow rate, a differential pressure and a PM-deposition amount.

The differential-based-deposition-amount calculator 41, which has a three-dimensional map showing a relationship among the calculated exhaust-gas flow rate V, the differential pressure DP and the PM-deposition amount, outputs the PM-deposition amount using the exhaust-gas flow rate V and the differential pressure DP as inputted values. FIG. 3 shows a relationship between the exhaust-gas flow rate V and the differential pressure DP obtained when the PM-deposition amount is a parameter. When the exhaust-gas flow rate V is constant, the PM-deposition amount increases with an increase in the differential pressure DP. When the differential pressure DP is constant, the PM-deposition amount decreases with an increase in the exhaust-gas flow rate V. For instance, as shown in FIG. 3, when the exhaust-gas flow rate is V1 and the differential pressure varies from DP1 to DP4, the PM-deposition amount correspondingly varies from P1 to P4. In other words, the PM-deposition amount P4 is larger than the PM-deposition amount P1. L1 to L4 are lines showing deposition levels of the PM-deposition amount. The differential-based-deposition-amount calculator 41 outputs the estimated PM-deposition amount (i.e., a differential-based deposition amount PMa) to the regeneration commander 43.

Model-Deposition-Amount Calculator

As shown in FIG. 2, based on information such as the intake mass flow rate, the fuel mass flow rate and the injection timing outputted from the engine controller 30 as well as the DPF temperature T outputted from the exhaust-gas-temperature sensor 74, the model-deposition-amount calculator 42 calculates a theoretical PM-deposition amount in accordance with a predetermined combustion model, and outputs the calculated PM-deposition amount (i.e., a model deposition amount PMb) to the regeneration commander 43.

In this manner, the model-deposition-amount calculator 42 can estimate the PM-deposition amount without using the differential pressure DP measured by the pressure sensor 733.

Regeneration Commander

The regeneration commander 43 commands the engine controller 30 to perform an automatic regeneration process depending on the differential-based deposition amount PMa calculated by the differential-based-deposition-amount calculator 41 or the model deposition amount PMb calculated by the model-deposition-amount calculator 42.

Further, when the deposition amount PMa or PMb exceeds a predetermined threshold PMth, the regeneration commander 43 outputs a command to the monitor 50 to show that manual forcible regeneration is necessary, and commands, when an operator requests manual forcible regeneration by operating the monitor 50, the engine controller 30 to control manual forcible regeneration.

Incidentally, according to the exemplary embodiment, the deposition level L4 as shown in FIG. 3 is used as the threshold PMth. Therefore, according to a normal control performed when the pressure measuring device 73 (FIG. 1) is usable, the regeneration commander 43 commands the monitor 50 to show that manual forcible regeneration is necessary when the differential-based deposition amount PMa calculated by the differential-based-deposition-amount calculator 41 exceeds the threshold PMth (i.e., the deposition level L4).

On the other hand, according to a model-based control performed when the malfunction determiner 46 determines that the pressure measuring device 73 is frozen to be unusable, the regeneration commander 43 commands the monitor 50 to show manual forcible regeneration is necessary when the model deposition amount PMb calculated by the model-deposition-amount calculator 42 exceeds the threshold PMth of PM-deposition amount calculated based on the combustion model.

Further, upon receipt of notification of completion of the manual forcible regeneration, the regeneration commander 43 commands the monitor 50 to show that the regeneration is completed.

Usability Determiner

The usability determiner 44 determines whether or not the pressure measuring device 73 (FIG. 1) is in a normal state, i.e., in a usable state.

Specifically, when it is detected that the PM-deposition amount derived from the exhaust-gas flow rate V and the differential pressure DP is a value less than the deposition level L1 (i.e., within a range R1) or a value within a range R2 beyond the deposition level L4, the usability determiner 44 determines the differential pressure DP measured by the pressure measuring device 73 is an unusual value and thus the pressure measuring device 73 is not in the normal state (i.e., the pressure measuring device 73 is unusable).

The usability determiner 44 outputs the determination result on whether the pressure measuring device 73 is usable or unusable to the malfunction determiner 46.

The reason for the usability determiner 44 to determine that the pressure measuring device 73 is unusable may be attributed to freezing or a failure in the pressure measuring device 73.

When the pressure measuring device 73 is determined to be unusable due to freezing, it may be considered that condensation water in the ducts 731, 732 is frozen to interfere with the introduction of the pressure of exhaust gas into the pressure measuring device 73 or that condensation water adhering to a pressure-receiving portion of the pressure sensor 733 is frozen to act on the pressure sensor 733 as an external force.

In both cases, the differential pressure DP measured by the pressure sensor 733 becomes an unusual value, so that the usability determiner 44 determines that the pressure measuring device 73 is unusable.

Similarly, for instance, when the pressure sensor 733 is in failure or the ducts 731, 732 are damaged, the differential pressure DP becomes an unusual value. In this case, the usability determiner 44 likewise determines that the pressure measuring device 73 is unusable.

Frozen-State Determiner

The frozen-state determiner 45 determines whether or not the pressure measuring device 73 is possibly frozen. The frozen-state determiner 45 makes a determination by comparing an atmospheric temperature Ta measured by the atmospheric-temperature sensor 75 provided at an appropriate position in the construction machine with a predetermined temperature Td. The frozen-state determiner 45 sets the predetermined temperature Td at a temperature at which the pressure measuring device 71 is unlikely to be frozen (e.g., 10 degrees C.).

When the atmospheric temperature Ta is lower than the predetermined temperature Td, the frozen-state determiner 45 determines that the pressure measuring device 73 is possibly frozen. When the atmospheric temperature Ta is not lower than the predetermined temperature Td, the pressure measuring device 73 is determined not to be frozen. The frozen-state determiner 45 outputs the determination result to the malfunction determiner 46.

Incidentally, the atmospheric temperature Ta is frequently used as a parameter for engine control and other controls, so that the atmospheric-temperature sensor 75 is usually originally equipped to a construction machine. Therefore, it is not necessary to provide another atmospheric-temperature sensor 75 for measuring the atmospheric temperature Ta used to determine whether or not the pressure measuring device 73 is frozen.

Malfunction Determiner

The malfunction determiner 46 determines whether or not the pressure measuring device 73 (FIG. 1) has a malfunction based on the determination result on the usability of the pressure measuring device 73 outputted from the usability determiner 44 and the determination result on whether or not the pressure measuring device 73 is frozen outputted from the frozen-state determiner 45. The malfunction determiner 46 outputs the determination result to the regeneration commander 43 and/or the malfunction notifier 47.

Specifically, when the usability determiner 44 determines that the pressure measuring device 73 is usable, the pressure measuring device 73 is determined to be in normal operation without any malfunction and the determination result is outputted to the regeneration commander 43. In this case, since the pressure measuring device 73 is in normal operation, the regeneration commander 43 performs regeneration control based on the differential-based deposition amount PMa calculated by the differential-based-deposition-amount calculator 41 using the differential pressure DP measured by the pressure sensor 733.

On the other hand, when the usability determiner 44 determines that the pressure measuring device 73 is unusable and the frozen-state determiner 45 determines that the pressure measuring device 73 is not frozen, the pressure measuring device 73 (the pressure sensor 733 and/or the ducts 731, 732) is determined to have a malfunction and the determination result is outputted to the engine controller 30, the regeneration commander 43 and the malfunction notifier 47.

When the pressure measuring device 73 is determined to have a malfunction, the regeneration commander 43 inhibits the regeneration process because the regeneration process are not to be appropriately performed. The malfunction notifier 47 commands the monitor 50 to display a caution to notify an operator of the malfunction of the pressure measuring device 73. The operator can then call a serviceperson and ask him/her to do maintenance on the pressure measuring device 73.

In consideration of the inhibition of the regeneration process and the necessity of reporting the malfunction to an operator who may miss the caution, the engine controller 30 decreases the output from the engine body 1 by a predetermined ratio.

When the usability determiner 44 determines that the pressure measuring device 73 is unusable and the frozen-state determiner 45 determines that the pressure measuring device 73 is frozen, the malfunction determiner 46 determines that the pressure measuring device 73 is frozen to be unusable and outputs the determination result to the regeneration commander 43. In this case, since the pressure measuring device 73 is frozen, the regeneration commander 43 performs the regeneration process in accordance with the model deposition amount PMb calculated by the model-deposition-amount calculator 42. However, it is not reported on the monitor 50 that the pressure measuring device 73 has a malfunction.

Malfunction Notifier

When the malfunction determiner 46 determines that the pressure measuring device 73 has a malfunction, the malfunction notifier 47 reports the malfunction of the pressure measuring device 73 on the monitor 50 so that an operator is notified of the malfunction.

Malfunction-Determining Method

Figure 4:
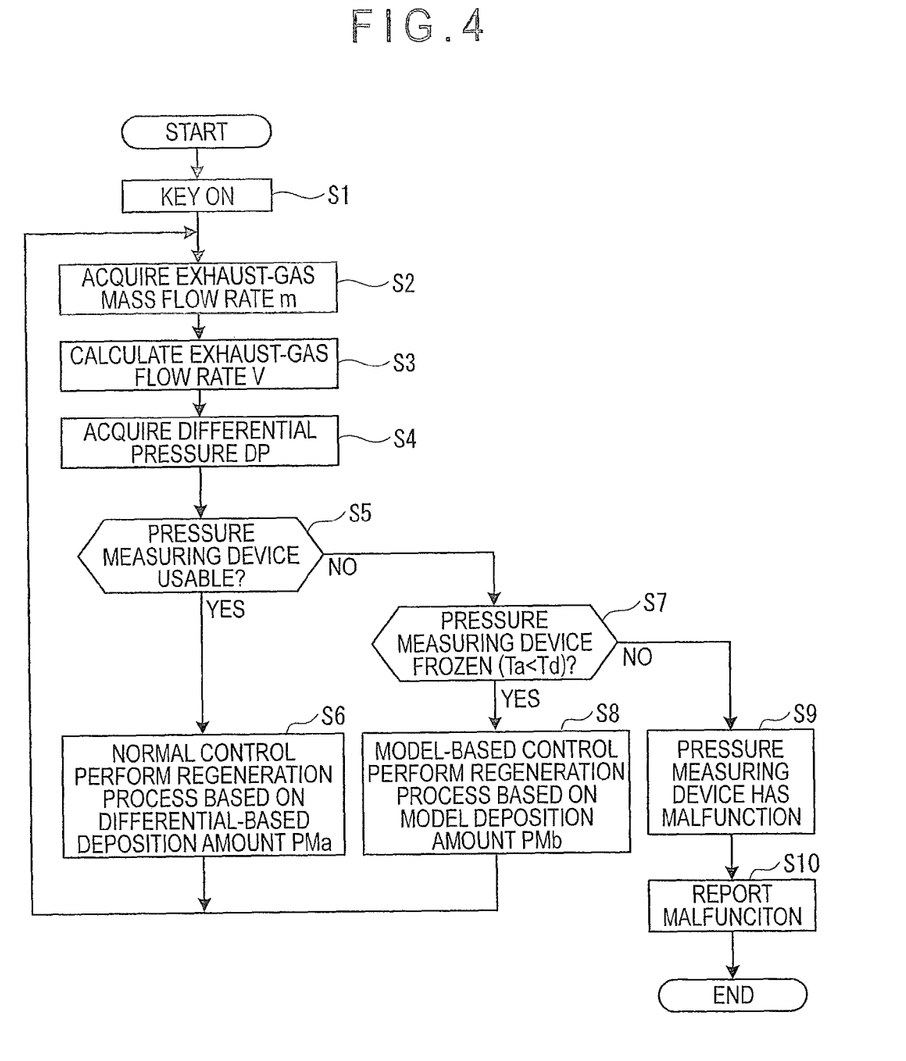
FIG. 4 is a flow chart for explaining a malfunction-determining method.

A malfunction-determining method for the exhaust gas purifying device 7 described with reference to FIGS. 1 to 3 will be described below with reference to FIG. 4. When an operator turns on a key to start the diesel engine 100, the engine controller 30 and the regeneration controller 40 are activated by power from a battery (step S1).

Subsequently, the differential-based-deposition-amount calculator 41 of the regeneration controller 40 (FIG. 1) calculates the differential-based deposition amount PMa. Specifically, the differential-based-deposition-amount calculator 41: acquires the exhaust-gas mass flow rate m (i.e., information on exhaust-gas flow rate) from the engine controller 30 (step S2); calculates the exhaust-gas flow rate V from the acquired exhaust-gas mass flow rate m, the DPF temperature T, the DPF-upstream pressure Pu and the gas constant R (step S3); and acquires the differential pressure DP from the pressure measuring device 73 (step S4).

Subsequently, the usability determiner 44 determines whether or not the pressure measuring device 73 is usable (step S5). Specifically, the usability determiner 44: determines that the pressure measuring device 73 is usable when a value based on the exhaust-gas flow rate V and the differential pressure DP lies within a range bounded between the deposition levels L1 and L4 in the map shown in FIG. 3 (Yes in step S5); or determines that the pressure measuring device 73 is unusable when the value lies within the range R1 below the deposition level L1 or within the range R2 beyond the deposition level L4 (No in step S5).

When the determination result is Yes in step S5, the regeneration controller 40 performs the normal control (step S6). Specifically, the determination result by the usability determiner 44 is outputted to the malfunction determiner 46 and the malfunction determiner 46 notifies the regeneration commander 43 that the pressure measuring device 73 is usable.

Since the pressure measuring device 73 is usable, the regeneration commander 43 performs the regeneration process in accordance with the differential-based deposition amount PMa calculated by the differential-based-deposition-amount calculator 41 based on the actual differential pressure DP measured by the pressure measuring device 73. The regeneration controller 40 then repeats the processes of steps S2 to S6.

When the determination result is No in step S5, the frozen-state determiner 45 determines whether or not the pressure measuring device 73 is frozen (step S7). Specifically, the frozen-state determiner 45: determines that the pressure measuring device 73 is frozen when the atmospheric temperature Ta measured by the atmospheric-temperature sensor 75 is lower than the predetermined temperature Td (Yes in step S7); or determines that the pressure measuring device 73 is not frozen when the atmospheric temperature Ta is not lower than the predetermined temperature Td (No in step S7).

When the determination result is Yes in step S7, the regeneration controller 40 performs the model-based control (step S8). Specifically, the determination result by the usability determiner 45 is outputted to the malfunction determiner 46 and the malfunction determiner 46 notifies the regeneration commander 43 that the pressure measuring device 73 is frozen to be unusable.

Since the pressure measuring device 73 is unusable, the regeneration commander 43 performs the regeneration process in accordance with the model deposition amount PMb calculated by the model-deposition-amount calculator 42. The regeneration controller 40 then repeats the processes of steps S2 to S8.

As time passes after the start of the diesel engine 100, the pressure measuring device 73 is getting heated by the heat of exhaust gas with frozen condensation water getting unfrozen. When the pressure measuring device 73 gets sufficiently unfrozen to be usable, the determination result becomes Yes in step S5, so that the normal control is then performed (step S6).

On the other hand, when the determination result is No in step S7, it means that the pressure measuring device 73 is unusable irrespective of the fact that the pressure measuring device 73 is less likely to be frozen. Therefore, the malfunction determiner 46 determines that the pressure measuring device 73 has a malfunction resulting from a failure in the pressure sensor 733 or damage to the ducts 731, 732 (step S9).

The malfunction notifier 47 then reports the malfunction on the monitor 50 (step S10). The operator can then call a serviceperson and ask him/her to do maintenance on the pressure measuring device 73. Further, the malfunction determiner 46 notifies the engine controller 30 and the regeneration commander 43 of the malfunction of the pressure measuring device 73. In consideration of the inhibition of the regeneration process and the necessity of reporting the malfunction to an operator who may miss the caution, the engine controller 30 decreases the output from the engine body 1 by the predetermined ratio.

When the malfunction of the pressure measuring device 73 is eliminated by serviceperson's maintenance and the key is again turned on, the processes of steps S1 and S2 and the subsequent steps are repeated.

According to the above-described exemplary embodiment, even when the usability determiner 44 determines that the pressure measuring device 73 is unusable, the malfunction determiner 46 does not determine that the pressure measuring device 73 has a malfunction as long as the frozen-state determiner 45 determines that the pressure measuring device 73 is frozen, so that the regeneration controller 40 continues the control based on the model deposition amount PMb calculated by the model-deposition-amount calculator 42. Therefore, the working vehicle can be kept in operation, thereby maintaining a favorable operation rate.

It should be appreciated that the scope of the invention is not limited to the above exemplary embodiment but modifications and improvements that are compatible with an object of the invention are included within the scope of the invention.

Figure 5:
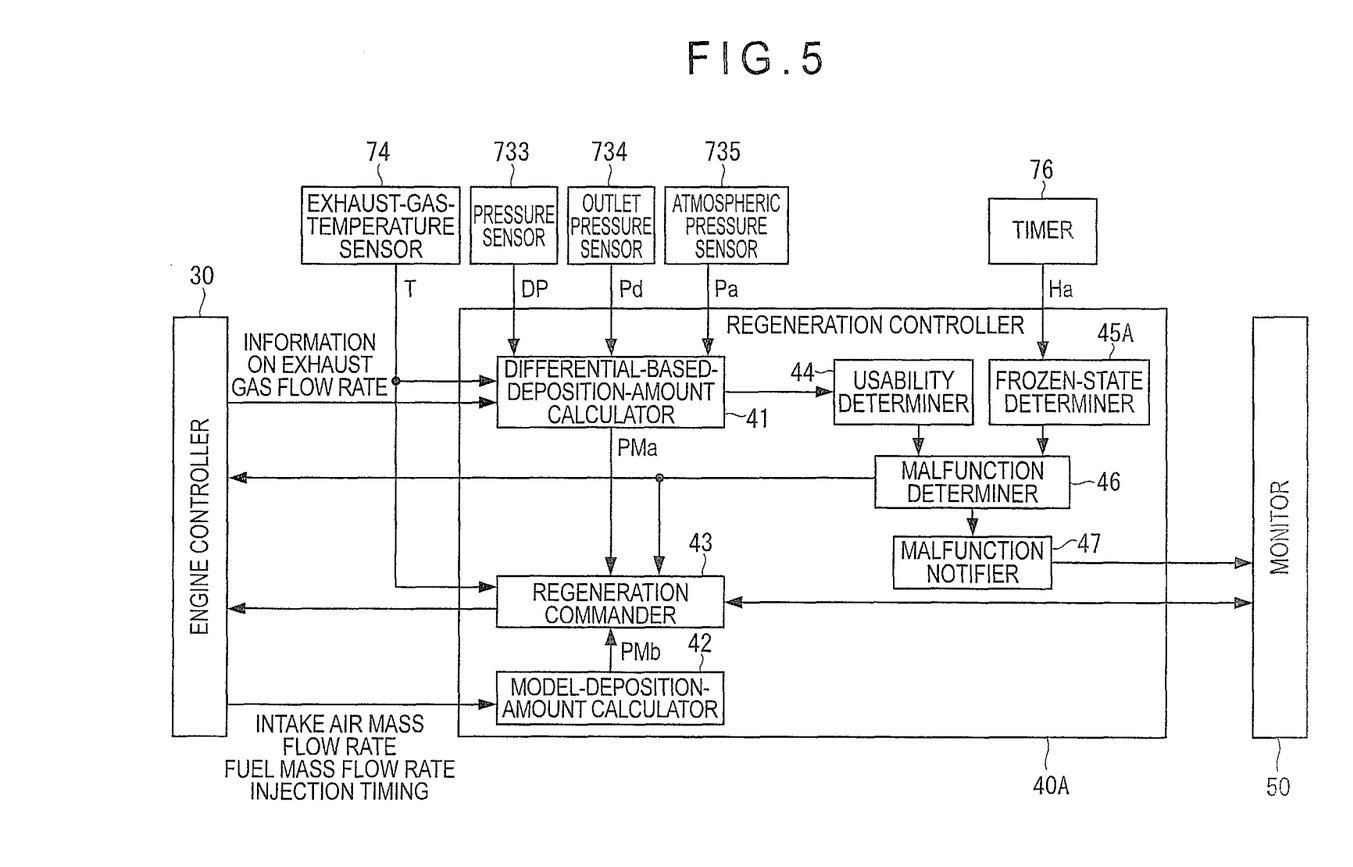
FIG. 5 is a block diagram showing a malfunction-determining device according to a modification of the exemplary embodiment.

In the exemplary embodiment, it is not requisite that the frozen-state determiner 45 determines whether or not the pressure measuring device 73 is frozen by comparing the atmospheric temperature Ta with the predetermined temperature Td. For instance, as shown in FIG. 5, a timer 76 configured to measure time elapsed since the diesel engine 100 is started (e.g., the key is turned on) may be provided in place of the atmospheric-temperature sensor 75 so that a frozen-state determiner 45A of a regeneration controller 40A determines that the pressure measuring device 73 is not frozen when a time Ha measured by the timer 76 exceeds a predetermined time Hd.

Figure 6:
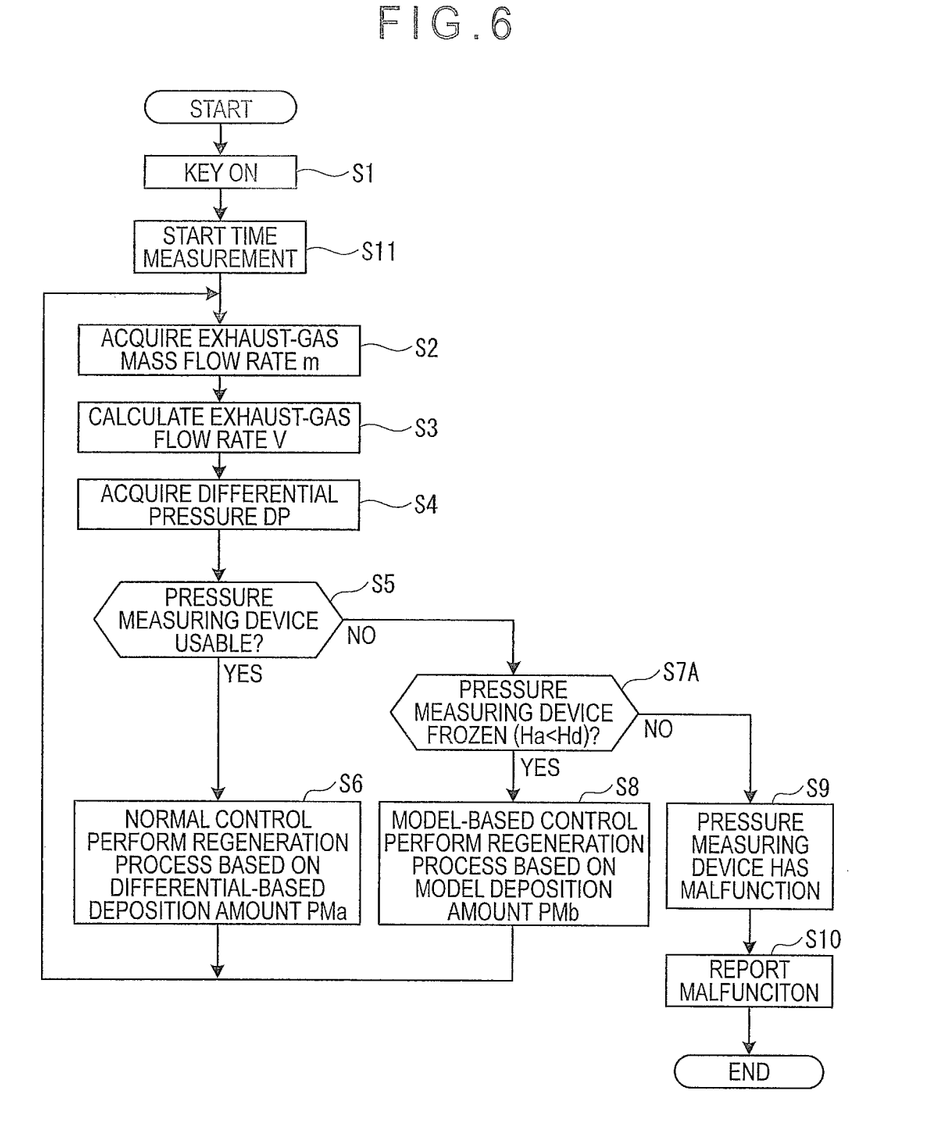
FIG. 6 is a flow chart showing the modification of the exemplary embodiment.

A process performed by the regeneration controller 40A according to the above modification is shown by a flow chart of FIG. 6. In FIG. 6, the same processes as ones in the flow chart of FIG. 4 according to the exemplary embodiment are denoted by the same reference signs to omit an explanation thereof As shown in FIG. 6, after the key is turned on in step S1, the timer 76 starts measuring time (step S11). When the determination result is No in step S5 and the time Ha measured by the timer 76 is less than the predetermined time Hd (Yes in step S7A), the frozen-state determiner 45A determines that the pressure measuring device 73 is possibly frozen and thus the model-based control is performed (step S8).

On the other hand, when the time Ha measured by the timer 76 is not less than the predetermined time Hd (No in step S7A), the pressure measuring device 73 is less likely to be frozen, so that the frozen-state determiner 45A determines that the malfunction of the pressure measuring device 73 is not due to freezing but due to a problem with the pressure measuring device 73 itself (step S9).

In view of the above, the predetermined time Hd may be set at a time sufficiently long for the pressure measuring device 73 in a frozen state to get unfrozen by, for instance, the heat of exhaust gas (e.g., eight hours). According to this modification, it can be determined whether or not the pressure measuring device 73 is frozen without using the atmospheric-temperature sensor 75, so that the invention is easily applicable to a vehicle or the like that is not equipped with the atmospheric-temperature sensor 75.

According to the exemplary embodiment, it is described that the atmospheric temperature Ta used to determine whether or not the pressure measuring device 73 is frozen is measured by the atmospheric-temperature sensor 75 that is originally equipped to the working vehicle, but another atmospheric-temperature sensor especially for determining whether or not the pressure measuring device 73 is frozen may be provided so that the determination is made based on the atmospheric temperature measured by this atmospheric-temperature sensor.

Alternatively, instead of using the atmospheric-temperature sensor 75, a temperature sensor may be provided to measure a temperature inside an engine compartment so that the temperature of the pressure measuring device 73 is estimated from the temperature measured by this temperature sensor and the pressure measuring device 73 is determined to be frozen or unfrozen based on the estimated temperature. Further alternatively, temperature sensors may be provided to directly measure temperatures of the pressure measuring device 73 (e.g., the temperatures of the pressure sensor 733 and the ducts 731, 732) so that the frozen-state determiner 45 determines whether or not the pressure measuring device 73 is frozen based on the temperatures measured by these temperature sensors.

A pressure measuring device to be subjected to the malfunction-determining process according to the exemplary embodiment may be different from the pressure measuring device 73. For instance, the process may be used to determine whether or not the outlet pressure sensor 734 has a malfunction. Further, when a selective catalytic reduction (SCR) is provided downstream of the DPF 72, the process may be used to determine whether or not a pressure measuring device provided to the SCR has a malfunction. In other words, the invention is usable to determine a malfunction of any pressure measuring device used in an exhaust gas purifying device.

The invention is applicable to working vehicles including construction machines such as hydraulic excavator, wheel loader and off-road dump truck, fixed power generators, and the like.

The invention claimed is:

1. A malfunction-determining device for an exhaust gas purifying device, the exhaust gas purifying device comprising: a filter device being provided in an exhaust passage for exhaust gas exhausted from an internal combustion engine to remove a residual substance in the exhaust gas; and a pressure measuring device being provided to the filter device to measure a pressure of the exhaust gas, the malfunction-determining device comprising:

a usability determiner being configured to determine whether or not the pressure measuring device is usable based on the pressure measured by the pressure measuring device and an exhaust gas flow rate;

a frozen-state determiner being configured to determine whether or not the pressure measuring device is frozen;

a malfunction determiner being configured to determine that the pressure measuring device has a malfunction when the usability determiner determines that the pressure measuring device is unusable and the frozen-state determiner determines that the pressure measuring device is not frozen; and a model-deposition-amount calculator being configured to calculate a theoretical amount of deposition of particulate matters in the filter device as a model-deposition-amount when the usability determiner determines that the pressure measuring device is not usable and the frozen-state determiner determines that the pressure measuring device is frozen.

2. The malfunction-determining device for the exhaust gas purifying device according to claim 1, the malfunction-determining device further comprising a malfunction notifier being configured to report the malfunction of the pressure measuring device when the malfunction determiner determines that the pressure measuring device has the malfunction.

3. The malfunction-determining device for the exhaust gas purifying device according to claim 1, wherein
the pressure measuring device is configured to measure a differential pressure in a filter used in the filter device between an inlet-side pressure and an outlet-side pressure of the exhaust gas, and
the usability determiner is configured to determine whether or not the pressure measuring device is usable based on the measured differential pressure and the exhaust gas flow rate.

4. The malfunction-determining device for the exhaust gas purifying device according claim 1, wherein
the frozen-state determiner comprises a temperature sensor configured to measure an atmospheric temperature or a temperature of the pressure measuring device and determines that the pressure measuring device is not frozen when the temperature measured by the temperature sensor is higher than a predetermined temperature.

5. The malfunction-determining device for the exhaust gas purifying device according claim 1, wherein
the frozen-state determiner comprises a timer being configured to measure time elapsed since the internal combustion engine is started and determines that the pressure measuring device is not frozen when the time measured by the timer exceeds a predetermined time.

6. A malfunction-determining method for an exhaust gas purifying device, the exhaust gas purifying device comprising: a filter device being provided in an exhaust passage for exhaust gas exhausted from an internal combustion engine to remove a residual substance in the exhaust gas; and a pressure measuring device being provided to the filter device to measure a pressure of the exhaust gas, the malfunction-determining method comprising:
determining whether or not the pressure measuring device is usable based on the pressure measured by the pressure measuring device and an exhaust gas flow rate;
determining whether or not the pressure measuring device is frozen after the pressure measuring device is determined to be unusable;
determining that the pressure measuring device has a malfunction when the pressure measuring device is determined not to be frozen; and
calculating a theoretical amount of deposition of particulate matters in the filter device as a model-deposition-amount when the usability determiner determines that the pressure measuring device is not usable and the frozen-state determiner determines that the pressure measuring device is frozen.

* * * * *